US012582545B1

(12) United States Patent
Furuta

(10) Patent No.: US 12,582,545 B1
(45) Date of Patent: Mar. 24, 2026

(54) CUP FOR AUTOMATIC EXCRETION TREATING APPARATUS AND AUTOMATIC EXCRETION TREATING APPARATUS

(71) Applicant: LIBERTYSOLUTION CO., LTD, Matsue (JP)

(72) Inventor: Miyuki Furuta, Matsue (JP)

(73) Assignee: LIBERTYSOLUTION CO., LTD, Matsue (JP)

( * ) Notice: Subject to any disclaimer, the term of this patent is extended or adjusted under 35 U.S.C. 154(b) by 311 days.

(21) Appl. No.: 18/263,460

(22) PCT Filed: Dec. 17, 2021

(86) PCT No.: PCT/JP2021/046843
§ 371 (c)(1),
(2) Date: Jul. 28, 2023

(87) PCT Pub. No.: WO2022/163205
PCT Pub. Date: Aug. 4, 2022

(30) Foreign Application Priority Data

Feb. 1, 2021 (JP) ................................. 2021-014382

(51) Int. Cl.
*A61F 5/451* (2006.01)
*A61F 5/44* (2006.01)
*A61F 5/442* (2006.01)

(52) U.S. Cl.
CPC ............ *A61F 5/451* (2013.01); *A61F 5/4404* (2013.01); *A61F 5/442* (2013.01)

(58) Field of Classification Search
CPC ........ A61F 5/451; A61F 5/4404; A61F 5/442; A61F 2013/15146; A61F 5/445; A61F 5/448; A61F 5/443
See application file for complete search history.

(56) References Cited

U.S. PATENT DOCUMENTS 4,747,166 A * 5/1988 Kuntz ..................... A61F 5/455
4/144.1
2003/0181880 A1 * 9/2003 Schwartz ................ A61F 5/442
604/358
(Continued)

FOREIGN PATENT DOCUMENTS

CN 102961226 A 3/2013
JP 2001224616 A 8/2001
(Continued)

OTHER PUBLICATIONS

Japan Patent Office, "Notice of Reasons for Rejection" From Application No. 2021-014382, mailed Jan. 28, 2025, pp. 8, With English Translation.
(Continued)

*Primary Examiner* — Susan S Su
*Assistant Examiner* — Erin A Kim
(74) *Attorney, Agent, or Firm* — Fredrikson & Byron, P.A.

(57) ABSTRACT

A cup for an automatic excretion treating apparatus provided in an automatic excretion treating apparatus configured to automatically perform excretion treatment of a person dependent on care includes a cup main body attached to the body of the person dependent on care and configured to receive excrement, and an expansion body provided between the cup main body and the body, expanding to be in close contact with the body by supplying with working fluid.

11 Claims, 5 Drawing Sheets

(56)  References Cited

U.S. PATENT DOCUMENTS

| | | |
|---|---|---|
| 2015/0328072 A1 | 11/2015 | Saitoh et al. |
| 2016/0278970 A1 | 9/2016 | Wei |
| 2017/0112658 A1 | 4/2017 | Hosono |

FOREIGN PATENT DOCUMENTS

| | | | |
|---|---|---|---|
| JP | 2006000288 A | | 1/2006 |
| JP | 2006055513 A | | 3/2006 |
| JP | 2008043500 A | | 2/2008 |
| JP | 2008048912 A | | 3/2008 |
| JP | 2008109998 A | * | 5/2008 |
| JP | 2016097257 A | | 5/2016 |
| JP | 2017153950 A | | 9/2017 |
| JP | U3217681 B2 | | 8/2018 |
| JP | 6635456 B | | 1/2020 |
| KR | 1020110080012 A | | 7/2011 |
| WO | 2013150588 A1 | | 10/2013 |

OTHER PUBLICATIONS

PCT International Search Report dated Mar. 1, 2022 for related International Application No. PCT/JP2021/046843, with English translation from which the instant application is based, 5 pgs.
National Intellectual Property Administration, PRC, "The First Office Action", From Application No. 202180091776.7, Dated Aug. 23, 2025, pp. 20.

* cited by examiner

1

CUP FOR AUTOMATIC EXCRETION TREATING APPARATUS AND AUTOMATIC EXCRETION TREATING APPARATUS

RELATED APPLICATIONS

This application is a 35 U.S.C. 371 national phase filing from International Application No. PCT/JP2021/046843, filed Dec. 17, 2021, which claims priority to Japanese Application No. 2021-014382, filed, Dec. 1, 2021, the contents of which are incorporated herein by reference.

TECHNICAL FIELD

The present invention relates to a cup for an automatic excretion treating apparatus and an automatic excretion treating apparatus configured to automatically treat excrement of those dependent on care.

Priority is claimed on Japanese Patent Application No. 2021-014382, filed Feb. 1, 2021, the content of which is incorporated herein by reference.

BACKGROUND ART

In recent years, those dependent on care such as aged persons and handicapped persons who need assistance for excretion treatment have been increasing year by year. While those dependent on care are increasing, there is a chronic shortage of nursing personnel. This trend is expected to become even more pronounced in the future. Excretion treatment of those dependent on care is the most burdensome for nursing staff. An automatic excretion treating apparatus has been proposed to assist in excretion of those dependent on care and reduce the burden on nursing staff.

The applicant has already proposed an automatic excretion treating apparatus and a cup for an automatic excretion treating apparatus that treats the excrement of those dependent on care (for example, see Patent Document 1 and Patent Document 2). The automatic excretion treating apparatus includes a cup attached to a body of a person dependent on care, a drainage apparatus configured to suction excrement in the cup and discharge the excrement through a sewage pipe, and a washing apparatus configured to supply rinse water from a water supply system to clean the inside of the cup and the body. According to the automatic excretion treating apparatus disclosed in Patent Document 1, the excrement can be discharged through a sewage line automatically while supplying water automatically upon excretion treatment and cleaning the body of the person dependent on care.

CITATION LIST

Patent Document

[Patent Document 1]
 Japanese Patent No. 6635456
[Patent Document 2]
 Japanese Unexamined Patent Application, First Publication No. 2017-153950

SUMMARY OF INVENTION

Technical Problem

Those dependent on care spend the day in various postures such as lying down, being turned over in bed, on a tilted bed having a raised upper half of the body, and the like. When those dependent on care are in the above-mentioned postures, a gap may occur between the cup that receives excrement and the body of the person dependent on care, and leakage of excrement or offensive odor may occur upon excretion treatment. According to the technology disclosed in Patent Document 1, even if there is a gap between the cup and the body, a leakage countermeasure during excretion treatment is performed by configuring a structure so that the air is sucked from the gap. The inventors have made further improvements in order to perform more reliable leakage countermeasures during excretion treatment under intensive research.

The present invention is directed to providing a cup for an automatic excretion treating apparatus and an automatic excretion treating apparatus that are capable of reducing leakage during excretion treatment.

Solution to Problem

An aspect of the present invention is a cup for an automatic excretion treating apparatus provided in an automatic excretion treating apparatus configured to automatically perform excretion treatment of a person dependent on care, which includes: a cup main body attached to the body of the person dependent on care and configured to receive excrement; and an expansion body provided between the cup main body and the body, expanding to be in close contact with the body by supplying with working fluid.

According to the present invention, since the expansion body is provided between the cup main body and the body of the person dependent on care, no gap is present between the cup main body and the body due to expanding the expansion body, and leakage of rinse water and excrement during excretion treatment can be reliably prevented.

In addition, the working fluid of the present invention may be supplied to the cup main body during excretion treatment.

According to the present invention, a configuration of the apparatus can be simplified without providing a specific apparatus by using air or rinse water during excretion treatment.

In addition, the working fluid of the present invention may be air supplied from an air supply apparatus configured to supply air into the cup main body during excretion treatment.

According to the present invention, the configuration of the apparatus can be simplified by expanding the expansion body using some of the air supplied to dry the inside of the cup main body during excretion treatment.

In addition, the working fluid of the present invention may be rinse water supplied from a washing apparatus configured to supply the rinse water into the cup main body during excretion treatment.

According to the present invention, the configuration of the apparatus can be simplified by expanding the expansion body using some of the rinse water supplied to clean the inside of the cup main body during excretion treatment.

In addition, the expansion body of the present invention may include a plurality of expansion chambers divided according to positions with which the body is in contact.

According to the present invention, the shape of the expansion body can be made easier to fit into the body by providing the plurality of expansion chambers in the expansion body.

In addition, the present invention may include a plurality of pressure sensors configured to detect pressures in the plurality of expansion chambers, respectively, and a control apparatus configured to individually change expansivity in the plurality of expansion chambers on the basis of the detection values of the plurality of pressure sensors.

According to the present invention, the shape of the expansion body can be made easier to fit into the body by individually changing expansivity of the plurality of the expansion chambers.

In addition, the present invention may include an adhesive layer provided between the expansion body and the body and configured to attach the expansion body and the body.

According to the present invention, leakage during excretion treatment can be reliably prevented by attaching the expansion body to the body with an adhesive layer.

In addition, the present invention may include an adhesion prevention layer formed on an inner wall of the cup main body and configured to promote separation between a treating target and the inner wall.

According to the present invention, since the adhesion prevention layer is formed on the inner wall of the cup main body, the treating target can be easily separated from the inner wall during excretion treatment, and probability of generating leakage during excretion treatment in which a treating time is reduced can be reduced.

In addition, an automatic excretion treating apparatus according to the present invention may include the above-mentioned cup for an automatic excretion treating apparatus.

According to the present invention, since the cup for an automatic excretion treating apparatus provided with the expansion body is provided in the automatic excretion treating apparatus, leakage in excretion treatment can be reliably reduced.

Advantageous Effects of Invention

According to the present invention, it is possible to reduce leakage during excretion treatment using the automatic excretion treating apparatus.

DESCRIPTION OF EMBODIMENTS

Hereinafter, an embodiment of an automatic excretion treating apparatus according to the present invention will be described with reference to the accompanying drawings.

The automatic excretion treating apparatus is configured to automatically perform excretion treatment for those dependent on care.

Figure 1:
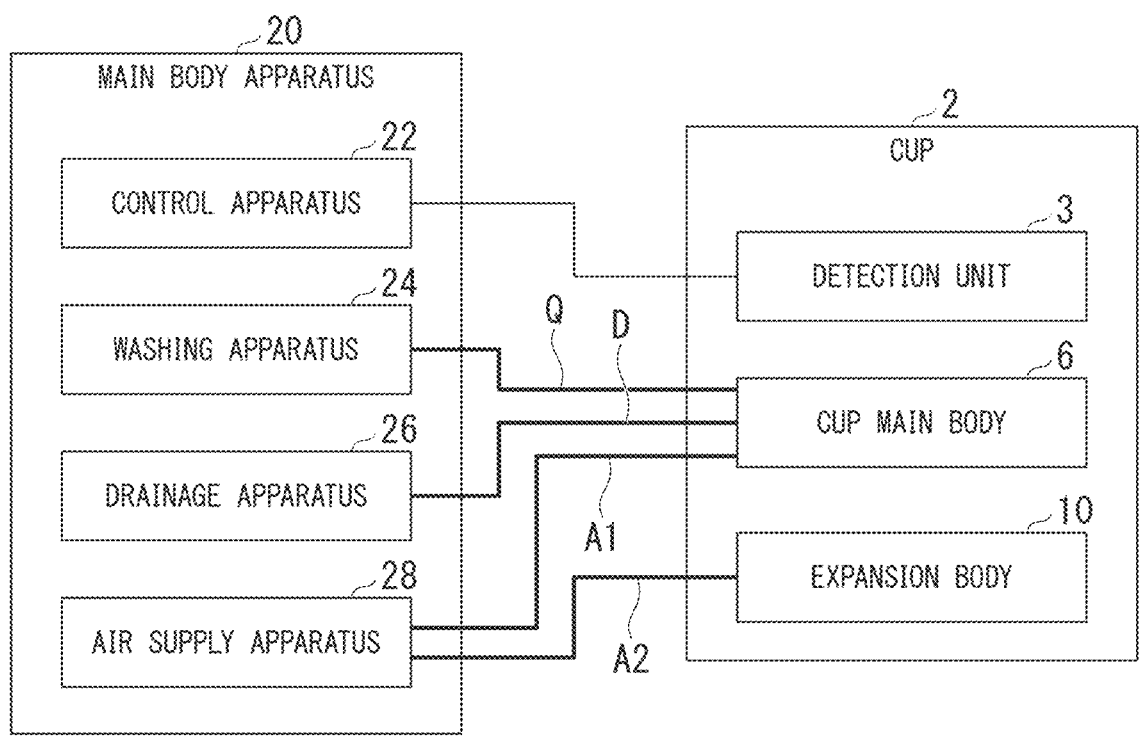
FIG. 1 is a block diagram showing a configuration of an automatic excretion treating apparatus according to an embodiment of the present invention.

As shown in FIG. 1, an automatic excretion treating apparatus 1 includes a cup 2 (a cup for an automatic excretion treating apparatus) attached to the body of a person dependent on care, and a main body apparatus 20 configured to clean the inside of the cup. The automatic excretion treating apparatus 1 is configured according to the automatic excretion treating apparatus disclosed in Patent Document 1. The automatic excretion treating apparatus 1 is not limited to this and may have other apparatus configurations.

The main body apparatus 20 includes a washing apparatus 24 configured to receive water supplied from a water supply system to clean the inside of the cup 2 and the body of the person dependent on care, a drainage apparatus 26 configured to discharge rinse water discharged from the inside of the cup 2 and waste water containing excrement through a sewage pipe, an air supply apparatus 28 configured to flow air into the cup 2, and a control apparatus 22 configured to control operations of each apparatus.

The cup 2 includes a detection unit 3 configured to detect excrement, a cup main body 6 attached to a periphery of the groin of the person dependent on care, and an expansion body 10 provided between the cup main body 6 and the body of the person dependent on care.

The control apparatus 22 is electrically connected to the detection unit 3, which will be described below, provided on the cup 2. The control apparatus 22 controls the washing apparatus 24, the drainage apparatus 26 and the air supply apparatus 28 on the basis of the detection values of the detection unit 3, discharges the water in the cup 2, and cleans and dries the inside of the cup 2.

The control apparatus 22 comprehensively controls the washing apparatus 24, the drainage apparatus 26 and the air supply apparatus 28, and executes cycles of excretion treatment. The control apparatus 22 is realized by executing a program (software) using a processor such as a central processing unit (CPU) or the like. Some or all of function parts of those may be realized by hardware such as a large scale integration (LSI), an application specific integrated circuit (ASIC), a field-programmable gate array (FPGA), or the like, or may be realized by cooperation of software and hardware.

The washing apparatus 24 is connected to the cup main body 6 by a water supply pipe Q. The washing apparatus 24 is controlled on the basis of the detection values to supply the rinse water supplied from the water supply system into the cup 2 via the water supply pipe Q. The washing apparatus 24 supplies a predetermined amount of rinse water set on the basis of the detection value to the cup 2.

The drainage apparatus 26 is connected to the cup main body 6 via a drain pipe D. The drainage apparatus 26 is controlled on the basis of the detection value to suction the rinse water and the excrement from the inside of the cup 2 via the drain pipe D, discharge the rinse water and the excrement to the outside of the cup 2, and discharge them through the sewage line.

The air supply apparatus 28 is connected to the cup main body 6 by an air supply pipe A1. The air supply apparatus 28 is controlled on the basis of the detection value to supply air into the cup main body 6 during excretion treatment. The air supply apparatus 28 supplies the air into the cup 2 via the air supply pipe A1 after the excrement is discharged from the cup 2 and the cup 2 is cleaned, and dries the inside of the cup 2 and the body of the person dependent on care. In addition, the air supply apparatus 28 is connected to the expansion body 10 by an air supply pipe A2. The air supply apparatus 28 is controlled on the basis of the detection value to supply the air into the expansion body 10. The air supply pipe A2 may be branched off from the air supply pipe A1 inside the cup 2. A valve (not shown) may be provided between the air supply pipe A1 and the air supply pipe A2. The valve is, for example, an electromagnetic valve whose opening and closing is controlled by the control apparatus 22 to adjust the supply amount of the air. The valve may be a proportional electromagnetic valve, an opening/closing amount of which is arbitrarily adjusted.

According to the configuration, excrement is temporarily caught in the cup 2, rinse water is supplied from the water supply system by the washing apparatus 24, and the body of the person dependent on care and the inside of the cup 2 are cleaned. In the cup 2, the rinse water and the excrement are discharged to the sewage line by the drainage apparatus 26. In the cup 2, the air is supplied by the air supply apparatus 28 after cleaning, and the body of the person dependent on care and the inside of the cup 2, which are cleaned, are dried.

The cup 2 includes the cup main body 6 attached to the body of the person dependent on care and configured to receive excrement. For example, the detection unit 3 configured to detect the excrement is provided inside the cup main body 6. The detection unit 3 is a capacitance sensor configured to electrically detect whether the excrement is solid or liquid. The detection value of the detection unit 3 is output to the control apparatus 22. A cycle of excretion treatment of the automatic excretion treating apparatus 1 is started on the basis of the detection result of the detection unit 3.

The expansion body 10 is provided between the cup main body 6 and the body of the person dependent on care. The expansion body 10 is controlled on the basis of the detection value, expands as the working fluid is supplied, and is in close contact with the body of the person dependent on care, when the excrement is detected in the cup main body 6. The working fluid is, tor example, air supplied by the air supply apparatus 28. A gap between the body of the person dependent on care and the cup 2 is removed by the expansion body 10 during excrement treatment, and leakage of excrement is greatly reduced.

Next, a specific shape of the cup 2 will be described. In the following description, an upward/downward direction of the cup 2 is defined in a state in which the cup is mounted in a posture in which the person dependent on care sleeps.

Figure 2:
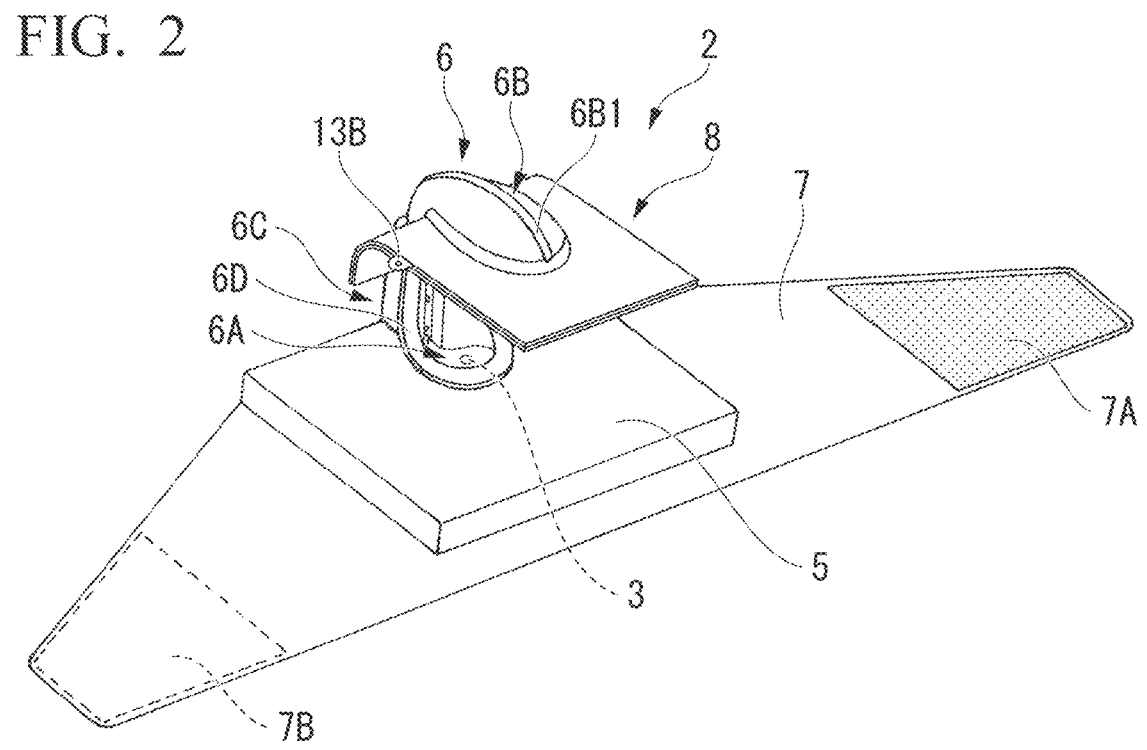
FIG. 2 is a perspective view showing a configuration of a cup for an automatic excretion treating apparatus.
Figure 3:
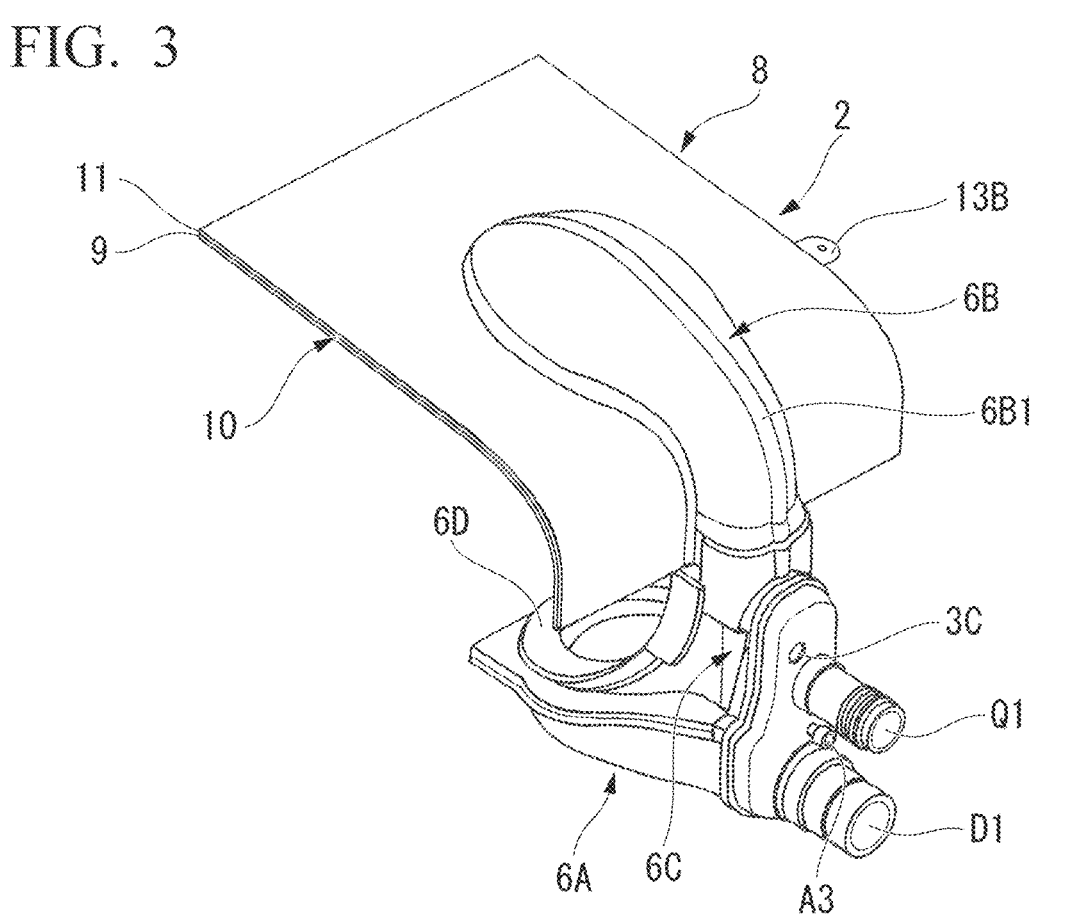
FIG. 3 is a perspective view showing a part of the configuration of the cup for an automatic excretion treating apparatus.

As shown in FIG. 2 and FIG. 3, the cup 2 includes the cup main body 6 which protrudes outward so as to cover surroundings of the groin and the anus of the person dependent on care and has an internal space. For example, the cup main body 6 has a first container 6A formed to cover surroundings of the anus of the person dependent on care, a second container 6B formed to cover surroundings of the groin of the person dependent on care, and a third container 6C configured to connect the first container 6A and the second container 6B and formed to cover the inguinal region of the person dependent on care. The cup main body 6 is integrally formed of, for example, a resin.

The cup main body 6 is formed to receive excrement and discharge the rinse water supplied from the washing apparatus and the excrement to the outside. An elastic member 6D with a curved cross section is formed on an edge that connects the first container 6A, the second container 6B and the third container 6C and extends along the edge. The elastic member 6D is formed of, for example, silicon rubber. The elastic member 6D comes into contact with the body to be elastically deformed, and reduces a gap generated between the edge of the first container 6A, the second container 6B and the third container 6C and the body.

The first container 6A is formed to expand downward and curve upward at a connecting portion to the third container 6C. For example, the detection unit 3 is provided in the first container 6A. A pad portion 5 configured to support the gluteal region of the person dependent on care is provided around the first container 6A. The pad portion 5 is formed in a plate shape. The pad portion 5 is formed of an elastic member such as sponge rubber or the like, a surface of which is covered with a waterproof sheet. The pad portion 5 is formed with an appropriate size greater than the gluteal region. The pad portion 5 has a notch that accommodates the first container 6A. The pad portion 5 is detachably formed in the first container 6A. The pad portion 5 is attached to or detached from the first container 6A and cleaned as appropriate.

The pad portion 5 is provided with a mounting/fixing member 7 that winds from the bottom surface of the pad portion 5 to the abdomen of the person dependent on care. The mounting/fixing member 7 is formed in a strip shape. Fixing portions 7A and 7B configured to fix both end portions to each other are provided on both end portions of the mounting/fixing member 7. The fixing portions 7A and 7B are constituted by, for example, a hook-and-loop fastener.

The third container 6C is formed to stand up in the upward/downward and bulge to cover the inguinal region. The third container 6C is provided with a connecting portion Q1 of the water supply pipe Q, a connecting portion D1 of the drain pipe D, a connecting portion A3 of the air supply pipe A1, and a connecting portion 3C of the detection unit 3. Through-holes in communication with an internal space of the third container 6C are formed in the connecting portion A3, the connecting portion Q1 and the connecting portion D1.

The second container 6B is formed to bulge upward and curve downward at a connecting portion with the third container 6C. An air flow passage 6B1 in communication with a flow passage for air in the connecting portion A3 is provided outside the second container 6B. The air flow passage 6B1 is formed to extend from a connecting portion between the second container 6B and the third container 6C to a tip portion of the second container 6B. The air flow passage 6B1 is blocked at the tip portion of the second container 6B. A plurality of air discharge openings (not shown) in communication with the inside of the second container 61 are formed in the middle of the air flow passage 6B1. When air is supplied from the air supply pipe A1 in a state in which the air supply pipe A1 is connected to the connecting portion A3, the air flows through the air flow passage 6B1, and the air is supplied into the second container 6B from the plurality of discharge openings. A lid portion 8 formed in a plate shape is provided around the second container 6B.

The lid portion 8 is formed in a plate shape around the second container 6B and curved downward at the connecting portion between the second container 6B and the third container 6C. The lid portion 8 covers a predetermined region around the second container 6B and reduces leakage of rinse water and excrement from surroundings of the second container 6B in a state in which the second container 6B is attached to the person dependent on care. The lid portion 8 is made of an elastic member such as a silicon resin so as to conform to the shape of the body of, for example, the person dependent on care. The lower surface side of the lid portion 8 is provided with the expansion body 10 which is freely expandable.

The expansion body 10 includes a bag body 11 that expands according to an inflow of a working fluid, and a contact layer 9 in contact with the body of the person dependent on care. The contact layer 9 is formed in substantially the same shape by the same elastic member as the lid portion 8. That is, the bag body 11 is formed to be sandwiched between the lid portion 8 and the contact layer 9. The lower surface side of the contact layer 9 has, for example, an adhesive force that exhibits predetermined adhesion when comes in contact with a human body surface upon mounting by a silicon resin and can be removed to the extent that it does not place a burden on the human body surface when removed. The contact layer 9 improves a degree of close contact between the cup 2 and the body of the person dependent on care. The expansion body 10 may be formed by the lid portion 8 and the contact layer 9. That is, the expansion body 10 may be formed integrally with the lid portion 8.

An adhesive layer configured to attach the expansion body and the body may be provided between the expansion body 10 and the body. That is, an adhesive layer having an adhesive force stronger than the adhesive force of the silicon resin may be formed on the side of the lower surface of the contact layer 9. The adhesive layer may have an adhesive force similar to that of, for example, an adhesive tape. The adhesive layer may be configured using a double sided tape or the like.

Figures 4, 5:
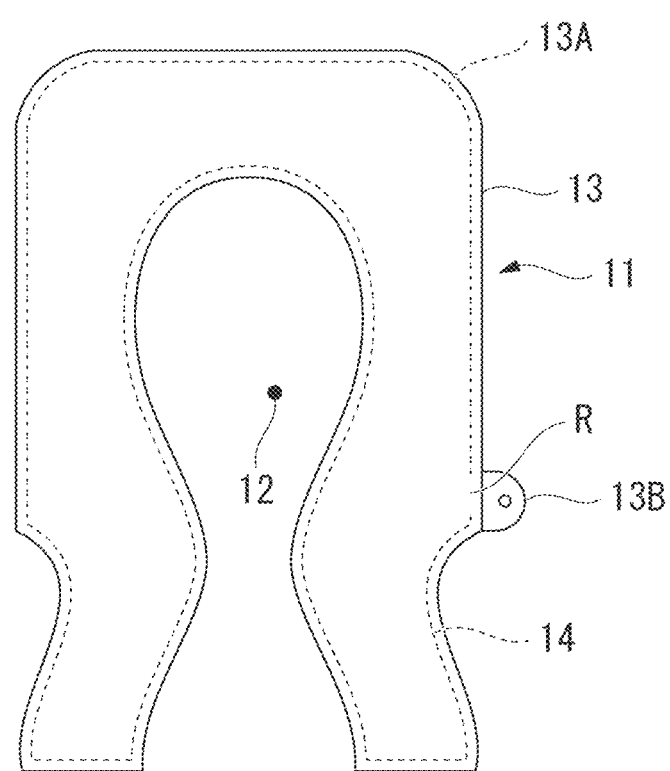
FIG. 4 is a plan view showing a configuration of a bag body.
FIG. 5 is a cross-sectional view showing a configuration of the bag body before expansion.

As shown in FIG. 4, the bag body 11 is formed in a sheet shape upon non-expansion. An upper surface side of the bag body 11 is adhered to a lower surface side of the lid portion 8. A lower surface side of the bag body 11 is adhered to an upper surface side of the contact layer 9. A cutout portion 12 that accommodates the second container 6B is formed in a central portion of the bag body 11. The bag body 11 is formed by a pair of resin sheet bodies 13 having thermoplasticity, for example, polyethylene or the like.

The bag body 11 is formed by the pair of sheet bodies 13 on the upper surface side and the lower surface aide. Outer edges of the two sheet bodies 13 become a welding portion 13A formed with a predetermined width through welding. A flow passage R that is not welded is formed in part of the outer edges of the two sheet bodies 13. A valve part 13B configured to supply a working fluid is continuously formed in the flow passage R. For example, the air supply pipe A2 is connected to the valve part 13B, and the air is supplied as the working fluid to the valve part 13B. According to the above-mentioned configuration, an expansion chamber is formed in the bag body 11.

Figure 6:
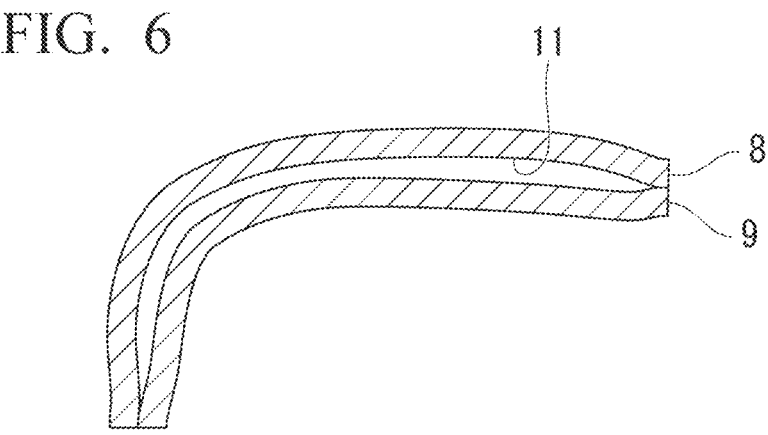
FIG. 6 is a cross-sectional view showing a configuration of the bag body after expansion.

As shown in FIG. 5, the bag body 11 is formed in a sheet shape upon non-expansion. As shown in FIG. 6, the bag body 11 is formed to expand when the working fluid is supplied during excretion treatment.

According to the above-mentioned configuration, the cup 2, in the state of being on the body of the person dependent on care, is supplied with air from the air supply apparatus 28 to the expansion body 10 through the air supply pipe A2 during excretion treatment, and the bag body 11 expands. As the bag body 11 expands, the contact layer 9 is pressed against the body of the person dependent on care. Since the expanded bag body 11 has flexibility and deforms according to the state of the body of the person dependent on care, the contact layer 9 is in close contact with the body of the person dependent on care without a gap.

The excrement in the cup main body 6 is treated in a state in which the expansion body 10 expands, and leakage of the rinse water and the excrement, and further, offensive odor in the cup main body 6, to the outside is prevented. In addition, the expansion body 10 is further expanded by a negative pressure generated in the cup main body 6 when the excrement is suctioned into the drain pipe D from the inside of the cup main body 6 during excretion treatment. Here, the degree of close contact between the expansion body 10 and the body of the person dependent on care is further increased, and generation of the gap is prevented. Since the expansion body 10 elastically deformed following the shape of the body of the person dependent on care even during expansion, occurrence of a gap between the cup main body 6 and the body of the person dependent on care is prevented by expansion of the expansion body 10 even when a posture of the body of the person dependent on care is changed. A regulator configured to adjust a pressure of the air supplied from the air supply apparatus 28 may be provided in the bag body 11 or the air supply pipe A2.

After the excretion treatment is completed and the operation of the air supply apparatus 28 is stopped, the expansion body 10 deflates as the air flows back through the air supply pipe A2. That is, since the expansion body 10 is configured to expand during excretion treatment, the burden on the body of the person dependent on care is reduced.

In the above embodiment, the expansion body 10 is provided in the lid portion 8 as an example, but the expansion body 10 may also be provided on the side of the gluteal region of the body of the person dependent on care. That is, the expansion body 10 may also be provided on the side of the upper surface of the pad portion 5.

The working fluid supplied to the bag body 11 may be rinse water supplied from the washing apparatus 24. In this case, the cup main body 6 may be connected to another water supply pipe separately from the water supply pipe Q from the washing apparatus 24, or may be connected to a water supply pipe for expansion branched off front the water supply pipe Q in the cup main body 6. An electromagnetic valve or the like may be provided between the water supply pipe Q and the water supply pipe for expansion, or a supply amount of rinse water to the bag body 11 may be adjusted by the control apparatus 22. The bag body 11 may be provided with a discharge opening configured to discharge the rinse water from the bag body 11 into the cup main body 6. The discharge opening may be formed by a hole formed in an aperture configured to eject rinse water while holding a water pressure in the bag body 11 within a predetermined range, or by a regulator.

[Variant 1]

Figure 7:
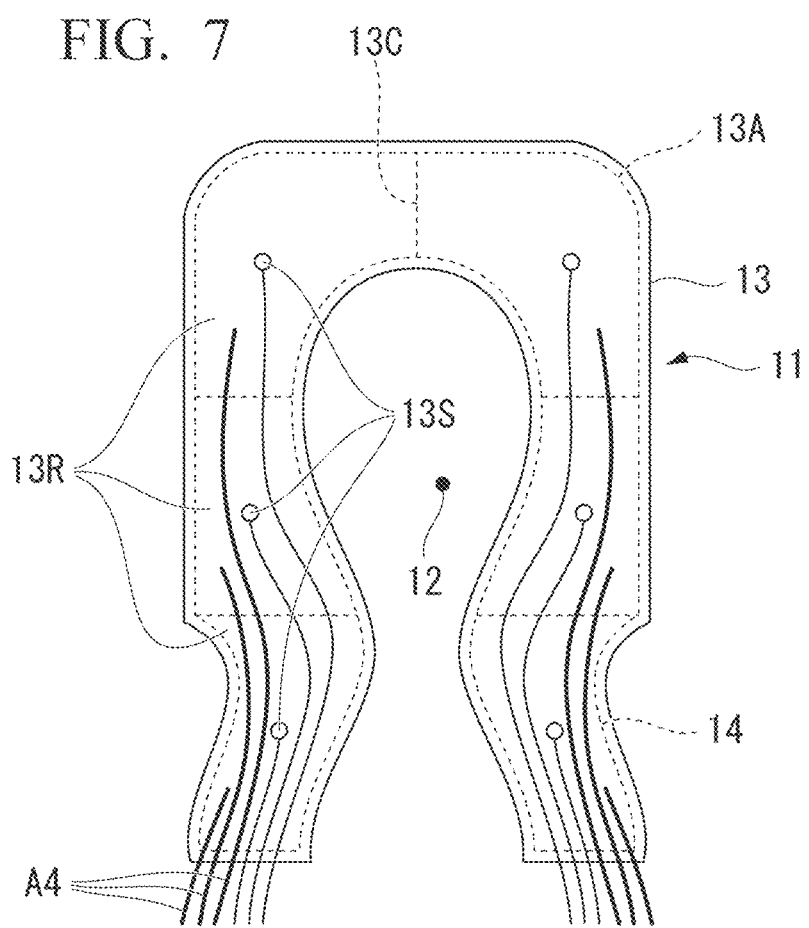
FIG. 7 is a plan view showing a configuration of a bag body according to Variant 1.

As shown in FIG. 7, the expansion body 10 may include a plurality of expansion chambers 13R divided according to positions with which the body is in contact. The plurality of expansion chambers 13R are separated by segments 13C each formed by welding. Pressure sensors 13S configured to detect an internal pressure are provided in the expansion chambers 13R, respectively. Air supply pipes A4 are individually connected to the expansion chambers 13R, respectively. The air is individually supplied into the plurality of air supply pipes A4 from the air supply apparatus 28, respectively. The air supply apparatus 28 is controlled by the control apparatus 22. The plurality of air supply pipes A4 may be branched off from the air supply pipe A1. In this case, a plurality of valves (not shown) may be provided between the plurality of air supply pipes A4 and the air supply pipe A1. Each valve is, for example, an electromagnetic valve whose opening and closing is controlled by the control apparatus 22 to adjust the supply amount of the air. Each valve may be a proportional electromagnetic valve whose opening/closing amount is arbitrarily adjusted.

The control apparatus 22 controls the air supply apparatus 28 and individually changes expansivity in a plurality of expansion chamber on the basis of the detection values of the pressure sensors 13S. According to the above-mentioned configuration, the control apparatus 22 can individually change the expansivity in the plurality of expansion chambers 3R according to the state of the body of the person dependent on care. That is, the control apparatus 22 can individually adjust expansivity in the plurality of expansion chambers 13R such that no excessive burden on a part of the body of the person dependent on care is generated on the basis of the detection values of the pressure sensors 13S. In addition, the control apparatus 22 can individually adjust expansivity of the plurality of expansion chambers 13R on the basis of the detection values of the pressure sensors 13S, holds the degree of close contact between the expansion body 10 and the body, and securely prevents leakage during excretion treatment, even when the body of the person dependent on care is moved during excretion treatment and the degree of close contact of the expansion body 10 is changed.

[Variant 2]

In order to prevent the leakage from the cup main body 6, it is also effective to form a shape of the cup main body 6 so as to shorten the time required for excretion treatment.

Figure 8:
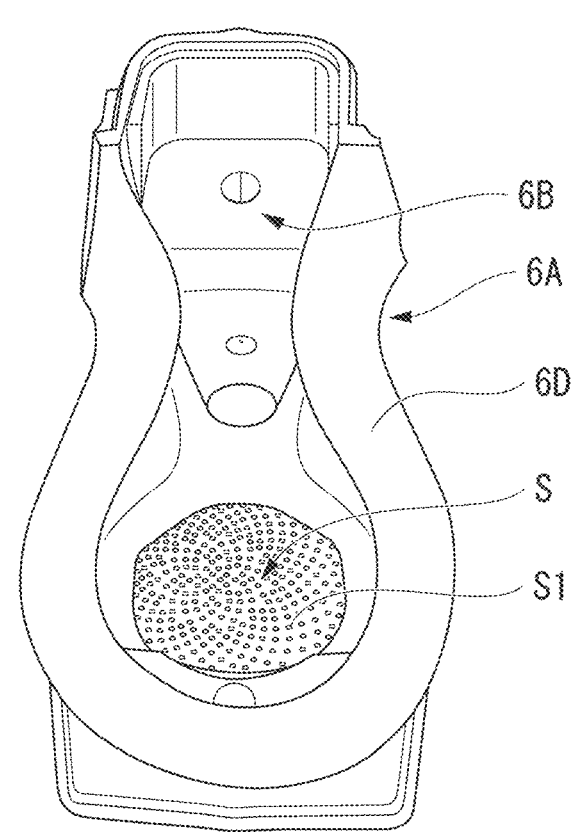
FIG. 8 is a view showing a configuration of an adhesion prevention layer according to Variant 2.

As shown in FIG. 8, an embossed adhesion prevention layer S having a plurality of dimple-shaped protrusions S1 is formed on an inner wall of the first container 6A of the cup main body 6. The adhesion prevention layer S may be formed not only on the first container 6A but also on the inner walls of the second container 6B and the third container 6C.

Figure 9:
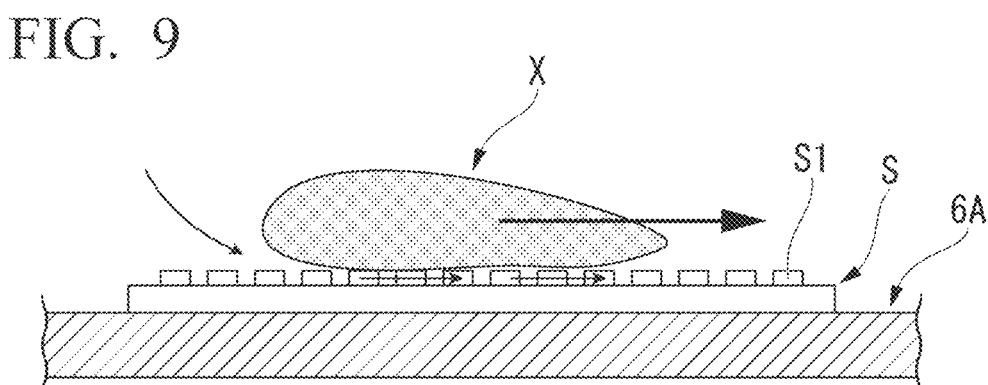
FIG. 9 is a cross-sectional view schematically showing an action of the adhesion prevention layer.

As shown in FIG. 9, as the adhesion prevention layer S is formed, a gap between solid or semi-solid excrement X (a treating target) and the inner wall of the first container 6A is increased to prevent adhesion between the excrement X and the inner wall of the first container 6A. As the adhesion prevention layer S is formed, rinse water or air easily flows between the excrement X and the inner wall of the first container 6A, separation between the excrement and the inner wall of the first container 6A can be promoted, and the excrement can be easily discharged to the outside of the cup main body 6.

By facilitating the excrement to be discharged out of the cup main body 6, the time required for excretion treatment can be shortened, and thus, probability of leakage of treated water and excrement from the cup main body 6 can be reduced. The adhesion prevention layer S may be formed not only by embossing but also by debossing with concave dimples, or may be formed by a chemical material layer that prevents adhesion such as fluorine resin processing.

As described above, according to the automatic excretion treating apparatus 1, as the expansion body 10 is provided in the cup 2, the degree of close contact between the body of the person dependent on care and the cup 2 can be improved to reliably prevent leakage during excrement treatment. According to the automatic excretion treating apparatus 1, the bag body 11 provided in the expansion body 10 has flexibility upon expansion and deforms according to the state of the body of the person dependent on care, and the gap between the body and the cup 2 can be reliably reduced. According to the automatic excretion treating apparatus 1, since the expansion body 10 expands during excretion treatment and deflates normally, a burden on the body of the person dependent on care can be prevented.

Hereinabove, while the embodiment of the present invention has been described, the present invention is not limited to the above-mentioned embodiment and may be appropriately changed without departing from the spirit of the present invention. For example, the expansion body 10 may be formed in a diaper type that can be integrated with or separated from the cup main body 6, or may further increase the degree of close contact. When the plurality of expansion chambers 13R are provided in the expansion body 10, the control apparatus 22 may perform mechanical learning using deep learning on the basis of the detection values of the pressure sensors 13S and individually adjust expansivity of the plurality of expansion chambers 13R optimally according to the state of the body of the person dependent on care. The detection values of the pressure sensors 13S from those dependent on care may be aggregated to a server in a hospital, a nursing facility, or the like, and the control apparatus 22 may perform mechanical learning using deep learning on the basis of the aggregated data.

REFERENCE SIGNS LIST

1 Automatic excretion treating apparatus
2 Cup
3 Detection unit
3C Connecting portion
5 Pad portion
6 Cup main body
6A First container
6B Second container
6B1 Air flow passage
6C Third container
6D Elastic member
7 Mounting/fixing member
7A, 7B Fixing portions
8 Lid portion
9 Contact layer
10 Expansion body
11 Bag body
12 Cutout portion
13 Sheet body
13A Welding portion
13B Valve part
13C Segment
13R Expansion chamber
13S Pressure sensor
20 Main body apparatus
22 Control apparatus
24 Washing apparatus
26 Drainage apparatus
28 Air supply apparatus
A1, A2, A4 Air supply pipe
A3 Connecting portion
D Drain pipe
D1 Connecting portion
Q Water supply pipe
Q1 Connecting portion
R Flow passage

The invention claimed is:

1. A cup for an automatic excretion treating apparatus provided in an automatic excretion treating apparatus configured to automatically perform excretion treatment of a person dependent on care, which comprises:

a cup main body attached to the body of the person dependent on care and configured to receive excrement; and an expansion body provided between the cup main body and the body, expanding to be in close contact with the body by supplying with working fluid, wherein the working fluid is rinse water supplied from a washing apparatus configured to supply the rinse water into the cup main body during excretion treatment.

2. The cup for an automatic excretion treating apparatus according to claim 1, wherein the working fluid is supplied to the cup main body during excretion treatment.

3. The cup for an automatic excretion treating apparatus according to claim 1, comprising an adhesive layer provided between the expansion body and the body and configured to attach the expansion body and the body.

4. The cup for an automatic excretion treating apparatus according to claim 1, comprising an adhesion prevention layer formed on an inner wall of the cup main body and configured to promote separation between a treating target and the inner wall.

5. A cup for an automatic excretion treating apparatus provided in an automatic excretion treating apparatus configured to automatically perform excretion treatment of a person dependent on care, which comprises:

a cup main body attached to the body of the person dependent on care and configured to receive excrement; and an expansion body provided between the cup main body and the body, expanding to be in close contact with the body by supplying with working fluid, wherein the expansion body includes a plurality of expansion chambers divided according to positions with which the body is in contact.

6. The cup for an automatic excretion treating apparatus according to claim 5, wherein the working fluid is air supplied from an air supply apparatus configured to supply air into the cup main body during excretion treatment.

7. The cup for an automatic excretion treating apparatus according to claim 5, wherein the working fluid is supplied to the cup main body during excretion treatment.

8. The cup for an automatic excretion treating apparatus according to claim 5, comprising an adhesive layer provided between the expansion body and the body and configured to attach the expansion body and the body.

9. The cup for an automatic excretion treating apparatus according to claim 5, comprising an adhesive prevention layer formed on an inner wall of the cup main body and configured to promote separation between a treating target and the inner wall.

10. An automatic excretion treating apparatus comprising the cup for an automatic excretion treating apparatus according to claim 5.

11. The automatic excretion treating apparatus according to claim 10, comprising a control apparatus, wherein the cup has a plurality of pressure sensors configured to detect pressures in the plurality of expansion chambers, respectively, and the control apparatus is configured to individually change expansivity in the plurality of expansion chambers on the basis of the detection values of the plurality of pressure sensors.

* * * * *